United States Patent
Konishi et al.

(10) Patent No.: US 10,053,716 B2
(45) Date of Patent: Aug. 21, 2018

(54) 4-AMINO CINNAMIC ACID PRODUCTION METHOD USING ENZYME

(71) Applicant: JAPAN SCIENCE AND TECHNOLOGY AGENCY, Saitama (JP)

(72) Inventors: Kazunobu Konishi, Okayama (JP); Naoki Takaya, Ibaraki (JP); Shunsuke Masuo, Ibaraki (JP); Shengmin Zhou, Ibaraki (JP)

(73) Assignee: JAPAN SCIENCE AND TECHNOLOGY AGENCY, Saitama (JP)

( * ) Notice: Subject to any disclaimer, the term of this patent is extended or adjusted under 35 U.S.C. 154(b) by 0 days.

(21) Appl. No.: 15/229,661

(22) Filed: Aug. 5, 2016

(65) Prior Publication Data

US 2016/0362711 A1    Dec. 15, 2016

Related U.S. Application Data

(63) Continuation of application No. PCT/JP2015/053412, filed on Feb. 6, 2015.

(30) Foreign Application Priority Data

Feb. 6, 2014    (JP) ................. 2014-021543

(51) Int. Cl.
| | | |
|---|---|---|
| C12P 13/00 | (2006.01) | |
| C07C 229/44 | (2006.01) | |
| C12N 9/88 | (2006.01) | |
| C12N 15/70 | (2006.01) | |

(52) U.S. Cl.
CPC .......... *C12P 13/005* (2013.01); *C07C 229/44* (2013.01); *C12N 9/88* (2013.01); *C12N 15/70* (2013.01); *C12Y 403/01024* (2013.01)

(58) Field of Classification Search
CPC . C12N 2310/14; C12N 15/111; C12N 15/113; C12N 2320/32; C12N 15/88; C12N 15/1037; C12N 15/86; C12N 2710/10043; C12N 15/1131; C12N 15/1138; C12N 9/88; C12N 15/52; C12N 2760/16134; C12N 9/1025; C12N 9/1029; C12N 15/1136; C12N 15/70; C12N 2310/11; C12N 2310/12; C12N 2310/141; C12N 2710/20034; C12N 2710/20071; C12N 2730/10134; C12N 2730/10171; C12N 2760/16171; C12N 2760/20134; C12N 2760/20171; C12N 7/00; C12N 9/003; C12N 9/52; C12P 13/222; C12P 13/005; C12P 13/225; C12P 13/24; C12P 17/06; C12P 7/42; C12P 7/62; C12P 13/001; C12P 13/22; C12P 21/06; C12Y 203/01; C12Y 403/01005; C12Y 403/01023; C12Y 105/01003; C12Y 304/21; C12Y 306/05002; C12Y 403/01024

See application file for complete search history.

(56) References Cited

U.S. PATENT DOCUMENTS

2002/0102712 A1    8/2002    Yoshida et al.
2014/0323679 A1    10/2014    Kaneko et al.

FOREIGN PATENT DOCUMENTS

| CN | 103060352 A | 4/2013 |
|---|---|---|
| EP | 3121275 A1 | 1/2017 |
| JP | 2005-511016 A | 4/2005 |
| WO | 2013/073519 A1 | 5/2013 |

OTHER PUBLICATIONS

Search Report dated Apr. 21, 2015 in PCT/JP2015/053412.
Chanh, N.B., et al., Thermal Behaviour and Room Temperature Crystal Structure of a Bidimensional Complex Salt of 4-Aminocinnamic Acid and Cadmium Chloride, Molecular Crystals and Liquid Crystals, 1990, vol. 188, pp. 261-271.
Bartsch, S., et al., Mutational analysis of phenylalanine ammonia lyase to improve reactions rates for various substrates, Protein Engineering, Design & Selection, 2010, vol. 23 No. 12, pp. 929-933.
Watts, K.T., et al., Discovery of a Substrate Selectivity Switch in Tyrosine Ammonia-Lyase, a Member of the Aromatic Amino Acid Lyase Family, Chemistry & Biology, Dec. 2006, pp. 1317-1326.
Zhu, L., et al., Cloning, expression and characterization of phenylalanine ammonia-lyase from Rhodotorula glutinis, Biotechnol. Lett., 2013, 35, pp. 751-756.
Suvannasara, P., et al., Biobased Polyimides from 4-Aminocinnamic Acid Photodimer, Macromolecules, Feb. 18, 2014, 47, pp. 1586-1593.
Yuta Kobayashi et al., "Keihisan to Keihisan Ruientai no Biseibutsu Seisan", Dai 66 Kai Abstracts of the Annual Meeting of the Society for Biotechnology, Japan, Aug. 5, 2014 (May 8, 2014), p. 127.
Yukiho Yamagata et al., "4-Amino Keihisan no Biseibutsu Henkan System no Kaihatsu", Japan Society for Bioscience, Biotechnology, and Agrochemistry Kanto Shibu 2012 Nendo Taikai Koen Yoshishu, Oct. 27, 2012 (Oct. 27, 2012), p. 60.
He, et al., "The gene cluster for chloramphenicol biosynthesis in Streptomyces venezuelae ISP5230 includes novel shikimate pathway homologues and a monomodular non-ribosomal peptide synthetase gene", Microbiology (2001),147,2001, pp. 2817-2829.
Yamagata, et al., "Development of microbial conversion system for 4-aminocinnamic acid", Lecture Abstracts from the 2012 General Meeting of the Japan Society for Bioscience, Biotechnology and Agrochemistry, Kanto Branch, 2012, 1 page (English machine translation included).
Gillessen, "Rekombinante Biosynthese amino-substituierter Phenylpropanoide in *Escherichia coli*", (with English Abstract), Apr. 9, 2009, 146 pages.

*Primary Examiner* — Rebecca E Prouty
(74) *Attorney, Agent, or Firm* — Perkins Coie LLP; Viola T. Kung

(57) ABSTRACT

This 4-amino cinnamic acid production method using the enzyme ammonia lyase can efficiently convert 4-amino phenylalanine into 4-amino cinnamic acid. This 4-amino cinnamic acid production method is characterized by converting 4-amino phenylalanine into 4-amino cinnamic acid by using phenylalanine ammonia-lyase, which comprises the amino acid sequence represented in sequence number 2 derived from the *Rhodotorula glutinis* yeast.

12 Claims, 5 Drawing Sheets

PAL ACTIVITY AND 4APAL ACTIVITY OF AtPAL4 AND ITS MUTANT ENZYMES

EFFECT OF pH ON NST37-pHSG298-AtPAL4 RESTING CELLS REACTION

EFFECT OF pH ON BL21-pET28a-RgPAL RESTING CELLS REACTION

(A) 4-AMINOCINNAMIC ACID PRODUCTION

(B) CINNAMIC ACID PRODUCTION

RgPAL AND AtPAL4 REACTIONS WITH PHENYLALANINE
AND 4-AMINOPHENYLALANINE AS SUBSTRATE

■ RgPAL
□ AtPAL4

(A)

(B)

PURIFICATION OF 4-AMINOCINNAMIC ACID
FROM RESTING CELLS REACTION SOLUTION

4-AMINO CINNAMIC ACID PRODUCTION METHOD USING ENZYME

This application is a continuation of PCT/JP2015/053412, filed Feb. 6, 2015, which claims priority of JP2014-021532, filed Feb. 6, 2014. The contents of the above-identified applications are incorporated herein by reference in their entirety.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence_Listing.txt with a creation date of Aug. 4, 2016, and a size of 28.7 kilobytes. The Sequence Listing filed via EFS-Web is part of the specification and is hereby incorporated in its entirety by reference herein.

TECHNICAL FIELD

The present invention relates to a method for producing 4-aminocinnamic acid using a specific ammonia lyase.

BACKGROUND ART

In recent years, in response to the problem of global warming caused by petroleum-derived carbon dioxide, opportunities continue to arise throughout the world to overhaul social structures that are overdependent on fossil fuels. This trend is leading to increasingly active operation of "biorefineries" that make use of bioprocessing technology, for which research is accelerating throughout the world, but unfortunately under the current state of affairs no research results have yet been obtained for biosynthesis of aromatic compounds, although in light of the importance of aromatic compounds for the chemical industry, diligent efforts are being expended in research toward synthesis of aromatic polymers.

For example, PTL 1 discloses a technique relating to polymer synthesis using 4-aminocinnamic acid as a natural molecule, and reports that a high heat-proof polymer is obtained from 4-aminocinnamic acid.

Also, as disclosed in NPL 1, the metabolic pathway for biosynthesis of 4-aminophenylalanine via shikimic acid has been elucidated (see p. 2818, FIG. 1), but there has been no disclosure nor teaching of ammonia lyase functioning in an organism and converting 4-aminophenylalanine to 4-aminocinnamic acid.

NPL 2 is aimed at production of a super engineering plastic starting material by microorganic conversion of glucose and production of 4-aminocinnamic acid as a highly reactive amine-based aromatic compound from the starting material, and a synthesis method for 4-aminocinnamic acid is being investigated utilizing 4-aminophenylalanine as a starting material and ammonia lyase as a catalyst, as illustrated by the following scheme:

[Chemical Formula 1]

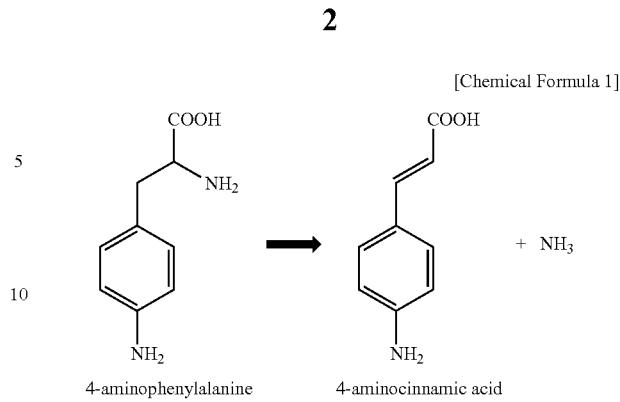

4-aminophenylalanine → 4-aminocinnamic acid + $NH_3$

It has already been reported that 4-aminophenylalanine can be fermentatively produced using glucose as the starting material.

Ammonia lyase, a member of the lyase family, is a specific enzyme that cleaves carbon-nitrogen bonds, and it is known that phenylalanine ammonia lyase (hereunder also abbreviated as "PAL") has the function of converting phenylalanine to cinnamic acid while tyrosine ammonia lyase has the function of converting tyrosine to 4-hydroxycinnamic acid.

NPL 2 reports that 0.12 g/L of 4-aminocinnamic acid was synthesized in resting cells reaction, using cells with *Arabidopsis thaliana*-derived ammonia lyase, but with such weak enzyme activity it is difficult for use as an industrial method. While *Arabidopsis thaliana*-derived ammonia lyase is one of the most commonly used ammonia lyases, it is not an enzyme suitable for 4-aminocinnamic acid synthesis from the viewpoint of enzyme activity that can be used for industrial production.

In addition, NPL 3 reports mutation analysis of PAL to improve the reaction rate on various substrates, but with 4-aminocinnamic acid, it is stated that it has an electron-withdrawing group on the benzene ring, and that conversion did not take place due to the presence of a positive mesomeric effect (see p. 930, right column, FIG. 2, p. 931, right column, Table II and p. 932, left column).

NPL 4, on the other hand, describes isolation of the gene for phenylalanine ammonia lyase of the yeast JN-1 *Rhodotorula glutinis* JN-1 (hereunder abbreviated as "RgPAL"), depositing of the yeast at CCTCC (China Center For Type Culture Collection) as deposit number M2011490, and creation of an optimum pH mutant by site-specific mutagenesis of the gene. Furthermore, since the Chinese Patent Application specification of which the authors of NPL 4 are the inventors (hereunder, PTL 2) was published on Apr. 24, 2013, the actual sequence of the RgPAL gene is publicly known. However, it is not disclosed that the enzyme can produce 4-aminocinnamic acid using 4-aminophenylalanine as the substrate.

Thus, there has not yet been established a production method that allows 4-aminocinnamic acid to be industrially mass-produced by an enzyme process, or an enzyme suited for such a method, and development thereof is strongly desired.

CITATION LIST

Patent Literature

[PTL 1] International Patent Publication No. WO2013/073519
[PTL 2] CN103060352A Specification

Non-Patent Literature

[NPL 1] He, et al., Microbiology (2001)
[NPL 2] Yamagata, Yukiho et al., "Development of microorganism conversion system for 4-aminocinnamic acid", Lecture abstracts from the 2012 General Meeting of the Japan Society for Bioscience, Biotechnology and Agrochemistry, Kanto Branch (p. 60).
[NPL 3] Bartsch, et al., Protein Engineering, Design & Selection, vol. 23, no. 12, pp. 929-933, 2010 [NPL 4] Zhou, et al., Biotechnol Lett (2013) 35:751-756

DISCLOSURE OF THE INVENTION

Problems to be Solved by the Invention

In light of the aforementioned prior art, the problem to be solved by the present invention is to provide a method for producing 4-aminocinnamic acid using the enzyme ammonia lyase (specifically, 4-aminophenylalanine ammonia lyase, hereunder, "4APAL") that can efficiently convert 4-aminophenylalanine as substrate to 4-aminocinnamic acid.

Means for Solving the Problems

As a result of measuring enzyme activity of ammonia lyase obtained from a wide variety of organisms, and diligent research and repeated experimentation directed toward selecting optimal enzymes, the present inventors have found that an enzyme having a specific amino acid sequence is suitable for conversion from 4-aminophenylalanine to 4-aminocinnamic acid, and the invention has been completed upon this finding.

Specifically, the present invention is as follows.

[1] A method for producing 4-aminocinnamic acid, wherein an enzyme selected from the group consisting of:
(a) proteins comprising the amino acid sequence listed as SEQ ID NO: 2;
(b) proteins comprising an amino acid sequence having at least 90% sequence identity with the amino acid sequence listed as SEQ ID NO: 2, and having 4-aminocinnamic acid synthesis activity;
(c) proteins comprising the amino acid sequence listed as SEQ ID NO: 2 with a deletion, substitution, insertion or addition of one or several amino acids, and having 4-aminocinnamic acid synthesis activity; and
(d) proteins encoded by a nucleic acid comprising a nucleotide sequence that hybridizes with a nucleic acid comprising a nucleotide sequence that is complementary with a nucleotide sequence coding for the amino acid sequence listed as SEQ ID NO: 2, under highly stringent conditions, and that codes for a protein having 4-aminocinnamic acid synthesis activity; is used to convert 4-aminophenylalanine to 4-aminocinnamic acid.

[2] The method according to [1] above, which comprises culturing or reacting resting cells of a microbe that produces the enzyme in a solution comprising 4-aminophenylalanine.

[3] The method according to [2] above, wherein the microbe is *Escherichia coli*.

[4] The method according to [2] or [3] above, wherein the resting cells reaction is conducted at pH 8 to pH 9.

[5] The method according to any one of [2] to [4] above, wherein the resting cells of *Escherichia coli* are selected from the group consisting of cultured cells, powdered cells and immobilized cells.

[6] The compound 4-aminocinnamic acid produced by the method according to any one of [1] to [5] above.

Effect of the Invention

Since, as demonstrated in the Examples, the enzyme of the invention has high activity of approximately 8-fold (see Example 3 and FIG. 5) with respect to ammonia lyase derived from *Arabidopsis thaliana*, and production on the order of several g/L was achieved, it therefore has high industrial applicability.

DESCRIPTION OF EMBODIMENTS

Figure 1:
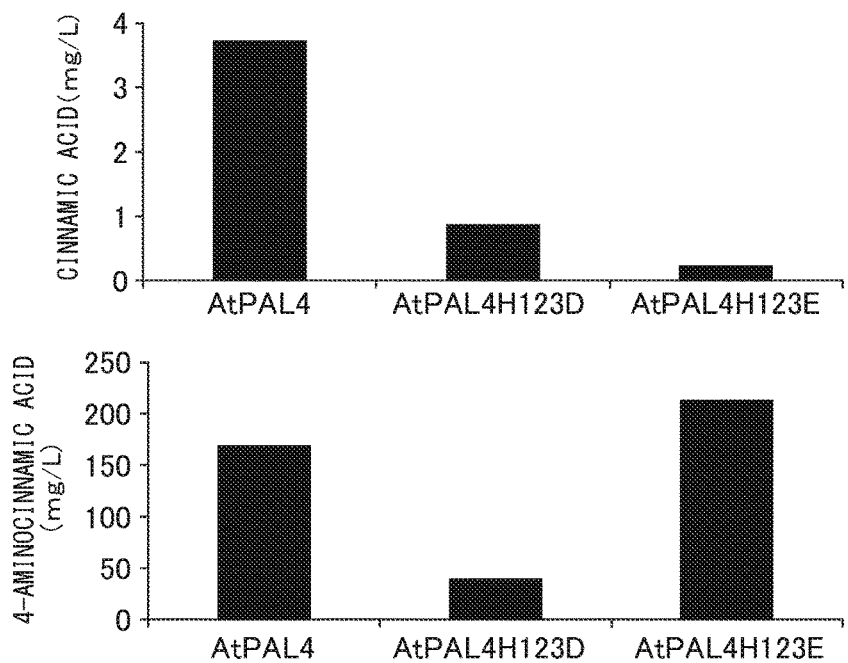
FIG. 1 is a set of graphs showing PAL activity and 4APAL activity for AtPAL4 and its mutant enzymes. (A): Resting cells reaction; (B) activity measurement.
Figure 1:
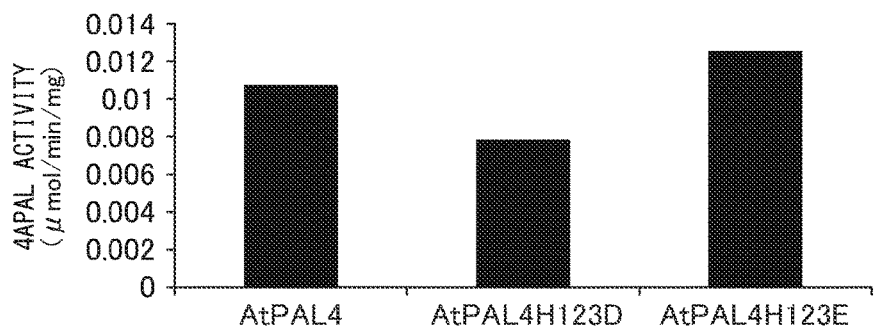

The invention will now be explained in detail by way of embodiments thereof.

According to the invention, the enzyme of interest is Phenylalanine Ammonia Lyase (PAL). PAL is an enzyme that has phenylalanine as its substrate and produces cinnamic acid. The difference between this reaction and the deammoniation reaction which is the object of the invention is the presence or absence an amino group at position 4 of the benzene ring. As mentioned above, NPL 3 states that with 4-aminocinnamic acid, it has an electron-withdrawing group on the benzene ring, and that conversion did not take place due to the presence of a positive mesomeric effect. In NPL 2, on the other hand, it is taught that despite very low enzyme activity, PAL derived from *Arabidopsis thaliana* exhibited 4APAL activity. Given this situation, the present inventors searched for enzymes with expectation for non-specificity of PAL substrate recognition. Since most of the PAL enzymes known to date are distributed among plants and basidiomycetous yeast, we decided to search among plant and basidiomycetous yeast PAL and select enzymes with high 4APAL activity. In addition, we conducted enzymatic analysis and production of 4-aminocinnamic acid by resting cells reaction using *Escherichia coli*.

As a result of the enzyme search, the present inventors found, unexpectedly, that yeast *Rhodotorula glutinis*-derived RgPAL has high PAL activity and 4APAL activity compared to plant *Arabidopsis thaliana*-derived AtPAL4, and confirmed the possibility of the production method of the invention using this specific enzyme.

Throughout the present specification, "resting cells" of bacteria means cells without bacterial growth such as, for example, cultured cells obtained by culturing the bacteria, powdered cells obtained by forming a powder by freezedrying or spray-drying the cultured cells, or immobilized cells obtained by immobilizing the cultured cells on a support, and by conducting reaction of at least one type of resting cells selected from among these, with the substrate 4-aminophenylalanine, it is possible to produce 4-aminocinnamic acid.

For example, a culture broth obtained by a culturing step may be subjected to centrifugal separation to separate the culture supernatant and the cells, and the cells then rinsed with physiological saline, suspended in sterilized purified water to a cell turbidity of $A_{600\,nm}=40$, and used as a resting cell suspension for reaction.

The present invention is a method for producing 4-aminocinnamic acid wherein an enzyme which is (a) a protein comprising the amino acid sequence listed as SEQ ID NO: 2 is used to convert 4-aminophenylalanine to 4-aminocinnamic acid.

As mentioned above, the full sequence of the RgPAL gene is publicly known from PTL 2, and SEQ ID NO: 2 of the present specification is identical to the amino acid sequence encoded by the RgPAL gene. Since a person skilled in the art can prepare a protein comprising the amino acid sequence listed as SEQ ID NO: 2 by any method known to those skilled in the art such as chemical synthesis, based on the sequence information provided, a person skilled in the art can obtain the protein and the present invention can be carried out regardless of the method in which it is obtained.

Furthermore, the protein of the invention also includes (b) a protein comprising an amino acid sequence having at least 90% sequence identity with the amino acid sequence listed as SEQ ID NO: 2, and having 4-aminocinnamic acid synthesis activity, and the sequence identity may be at least 91%, 92%, 93%, 94%, 95%, 96%, 97%, 98% or 99%.

Here, the term "sequence identity" means, for two chains of polypeptide sequences (or amino acid sequences) or polynucleotide sequences (or nucleotide sequences), the quantity (number) of amino acid residues or nucleotides composing them that can be determined as identical between the two chains, in terms of the mutual agreement between them, meaning the degree of sequence correlation between two polypeptide sequences or two polynucleotide sequences. Identity can be easily calculated. Numerous methods are known for measuring identity between two polynucleotide sequences or polypeptide sequences, and the term "sequence identity" is well known to those skilled in the art.

Furthermore, the protein of the invention also includes (c) a protein comprising the amino acid sequence listed as SEQ ID NO: 2 with a deletion, substitution, insertion or addition of one or several amino acids, and having 4-aminocinnamic acid synthesis activity. Here, "several" may be at most 10, 9, 8, 7, 6, 5, 4, 3 or 2.

Mutant DNA can be prepared by any method known to those skilled in the art such as, for example, chemical synthesis, genetic engineering or mutagenesis. Specifically, DNA comprising the nucleotide sequence listed as SEQ ID NO: 1 which codes for the amino acid sequence listed as SEQ ID NO: 2 may have a mutation introduced into the DNA using a method of contact with a chemical agent serving as a mutagen, a method of irradiation with ultraviolet rays or a genetic engineering method, to obtain mutant DNA. Site-specific mutagenesis is a genetic engineering method that is useful as it allows introduction of specific mutations into specified sites, and it may be carried out by the method described in Sambrook, J. et al., Molecular Cloning: A Laboratory Manual, $2^{nd}$ Ed., Cold Spring Harbor Laboratory Press, Cold Spring Harbor, N.Y., 1989. By producing the mutant DNA using a suitable production system, it is possible to obtain a protein comprising an amino acid sequence with a deletion, substitution, insertion or addition of one or several amino acids.

In addition, the protein of the invention includes (d) a protein encoded by a nucleic acid comprising a nucleotide sequence that hybridizes with a nucleic acid comprising a nucleotide sequence that is complementary with a nucleotide sequence coding for the amino acid sequence listed as SEQ ID NO: 2, under highly stringent conditions, and that codes for a protein having 4-aminocinnamic acid synthesis activity.

As used herein, "stringent conditions" are conditions that allow specific binding between a polynucleotide and genomic DNA in a selective and detectable manner. Stringent conditions are defined by an appropriate combination of salt concentration, organic solvent (for example, formamide), temperature and other known conditions. Specifically, stringency is increased by reducing the salt concentration, increasing the organic solvent concentration or raising the hybridization temperature. Stringency is also affected by the rinsing conditions after hybridization. The rinsing conditions are defined by the salt concentration and temperature, and stringency of rinsing is increased by reducing the salt concentration and raising the temperature. Thus, "stringent conditions" means conditions in which a specific hybrid is formed only between nucleotide sequences having high identity, namely a degree of identity between the nucleotide sequences of about 90% or greater as the overall average. Specifically, "stringent conditions" indicates hybridization with 6.0×SSC at about 45° C. followed by rinsing with 2.0×SSC at 50° C. For selection of stringency, the salt concentration in the rinsing step may be selected between, for example, about 2.0×SSC, 50° C. as low stringency to about 0.1×SSC, 50° C. as high stringency. Also, the temperature for the rinsing step may be raised from room temperature, or approximately 22° C., as low stringent conditions to about 65° C. as high stringent conditions. The hybridization can be carried out according to a method known to those skilled in the art or a similar method. When a commercially available library is to be used, it may be carried out according to the method described in the accompanying directions for use.

As used herein, "nucleic acid" includes ribonucleic acid, deoxyribonucleic acid, and any modified forms of nucleic acids. Nucleic acids include both single-stranded and double-stranded forms. The nucleic acid (gene) of the invention can be prepared by any method known to those skilled in the art, using primers or probes constructed based on the nucleotide sequence disclosed in a database of an authority known to those skilled in the art, or in the present specification. For example, by using a PCR method or another DNA amplification technique known to those skilled in the art, it is possible to easily obtain the cDNA for a gene. Alternatively, a person skilled in the art can synthesize nucleic acid using suitable known technology based on the sequence information disclosed herein. A nucleic acid (gene) encodes a protein. Here, "encodes" means that it allows production of the protein of the invention in a state in which it exhibits its activity. Also, the term "encodes" includes both encoding a structural sequence (exon) that is a continuous section of the protein of the invention, or encoding the protein via an appropriate intervening sequence (intron).

As will be explained in detail in the Examples that follow, it was demonstrated that yeast *Rhodotorula glutinis*-derived RgPAL has high PAL activity and 4APAL activity compared to plant *Arabidopsis thaliana*-derived AtPAL4. When resting cells reaction was conducted using recombinant *Escherichia coli* producing these two types of PAL, attempting conversion from 4-aminophenylalanine to 4-aminocinnamic acid, high conversion efficiency was found at pH 8 or pH 9. This is assumed to be because, the base dissociation constant $pK_b$ of aniline being 9.40, ionization of the amino group at position 4 of the benzene ring increases affinity between 4-aminophenylalanine and the enzyme.

For AtPAL4, when the amino acid associated with amino acid substrate recognition was mutated from histidine to glutamic acid or aspartic acid, mutation to glutamic acid reduced PAL activity while increasing 4APAL activity, suggesting increased selectivity for 4-aminophenylalanine. Mutation to aspartic acid, on the other hand, clearly decreased both PAL activity and 4APAL activity compared to the wild type. Histidine and aspartic acid have main chains of four carbons while glutamic acid has a main chain of five carbons. It is expected that the binding rate to substrate increased because of the main chain that is longer by one carbon atom.

When the production level of PAL by *Escherichia coli* was examined using a crude cell extract, it was found that RgP AL was produced at about a 30-fold amount compared to other PAL. Also, when the Km value of the purified enzyme for 4-aminocinnamic acid was measured, it was found to be 22 mM with RgPAL, which was lower than AtPAL4 and mutant enzyme. This agrees the results of maximized 4-aminocinnamic acid production when using RgPAL-transferred *Escherichia coli* in resting cells reaction.

With the invention, 4-aminocinnamic acid was successfully produced at a maximum of 825 mg/L in resting cells reaction using the enzyme RgPAL.

EXAMPLES

The present invention will now be explained in detail using examples and comparative examples.

The following materials and methods were used in the examples and comparative examples.

[Measurement of Enzyme Activity of *Escherichia coli* Recombinant Enzyme Crude Extract]

*Escherichia coli* was inoculated into 5 ml of LB medium containing 100 mg/L ampicillin sodium or 100 mg/L kanamycin sulfate, and cultured overnight at 37° C. It was then inoculated into 200 ml of the same culture medium and cultured to an O.D. of 0.6, isopropyl-β-thiogalactopyranoside (IPTG) was added to a final concentration of 0.5 mM, and culturing was conducted for 12 hours at 28° C.

The cultured cells were collected and suspended in 20 mM potassium phosphate buffer (pH 7.5) and subjected to ultrasonic disruption and the supernatant was used as a crude extract for activity measurement. The enzyme activity was measured and quantified by measuring the absorbance at the absorption wavelength of the reaction product using a spectrophotometer, for a period of 5 minutes. For PAL activity, the crude extract was added to 100 mM Tris Buffer (pH 8.0) and 20 mM phenylalanine, reaction was conducted, and production of cinnamic acid was measured by the change in absorbance at a wavelength of 290 nm, while for 4APAL activity, 20 mM 4-aminophenylalanine was used as substrate and the absorbance at a wavelength of 315 nm due to 4-aminocinnamic acid was measured and quantified.

[Measurement of Enzyme Activity of *Escherichia coli* Recombinant Purified Enzyme]

*Escherichia coli* was inoculated into 5 ml of LB medium containing 100 mg/L ampicillin sodium or 100 mg/L kanamycin sulfate, and cultured overnight at 37° C. It was then used to inoculate 200 ml of the same culture medium and cultured to an O.D of 0.6, IPTG was added to a final concentration of 0.5 mM, and the incubation was continued for 12 hours at 28° C. The rotational speed during cultures was 120 rpm. The cultured cells were collected and suspended in 20 mM potassium phosphate buffer (pH 7.5) and subjected to ultrasonic disruption, and after centrifugal separation, the supernatant was purified using a His-Trap column and the enzyme activity was measured. The method of measuring the enzyme activity was according to the method for the crude extract described above.

[Resting Cell Reaction]

(1) Preculture

*Escherichia coli* was cultured at 37° C. using LB medium containing 100 mg/L ampicillin sodium or 100 mg/L kanamycin sulfate. One platinum loop of the cells was transferred from pregrown agar medium to a test tube containing 5 ml of culture medium, and shake-culture was conducted overnight at 120 rpm.

(2) Main Culturing

The precultured cells were transferred at 1% into 200 ml of the same medium in a baffle-equipped flask. Shake-culture was conducted at 37° C., a prescribed amount of IPTG was added at the point when the O.D. of the culture broth reached 0.3, and the culture was conducted at 28° C. for 12 hours to induce production of the target gene.

(3) Reaction Method

The main cultured cells were collected and rinsed once with 50 mM KPi Buffer (pH 7), and then suspended in 5 ml of a reaction mixture containing 20 mM substrate (4-aminophenylalanine, phenylalanine), for resting cell reaction. The reaction was conducted for 0 to 24 hours while shaking at 37° C. After the reaction, the supernatant was transferred to a centrifuge tube and recovered by centrifugal separation, and high-performance liquid chromatography (HPLC) was used in the following manner for quantitation of the reaction product.

(4) Quantitation Method

HPLC (1200 infinity series: Hewlett Packard) was used for quantitation. A Purospher STAR RP-18 endcapped column was used, with a mixture of 20 mM potassium phosphate (pH 7.0) and 100% methanol as the eluent. Measurement was carried out using absorption at wavelengths of 210 nm, 254 nm and 280 nm.

[Strains Used]

As *Escherichia coli* strains there were used NST37 [ATCC 31882, U.S. Pat. No. 4,681,852, genotypes: aroG, aroF, pheA, tyrR, ryrA, trpE] and BL21(DE3) [Novagen, genotypes: F⁻, ompT, $hsdS_B$ ($r_B^-m_B^-$), gal (λcI857, ind1, Sam7, nin5, lacUV5-T7 gene1), dcm(DE3)].

[Medium Composition (/L)]

The medium compositions used are listed in Table 1. The culture media used were sterilized at 121° C., 15 minutes using an autoclave.

TABLE 1

| LB medium pH 7.0 | |
| --- | --- |
| Tryptone | 10 g/L |
| Yeast extract | 5 g/L |
| NaCl | 10 g/L |

[Culturing Conditions]

*Escherichia coli* was cultured in LB medium at 37° C. Preculture was conducted using a test tube containing 5 ml of medium, and main culture was accomplished by placing 200 ml of medium in a baffle-equipped flask, adding 1% of the preculture broth, and shake-culturing at 120 rpm under the same conditions as the preculture.

[Construction of Plasmids]

(1) Preparation of pHSG298-AtPAL4

PAL derived from the plant *Arabidopsis thaliana* (GenBank GI:30681254, gene locus: AT3G10340, nucleotide sequence listed as SEQ ID NO: 3, amino acid sequence listed as SEQ ID NO: 4) was amplified by PCR using two primers (5'-CCGGATCCATGGAGCTATGCAAT-CAAAACAATC-3' and 5'-CCGCATGCTCAACAGATT-GAAACCGGAGCTCCG-3'), and was then treated with BamHI and SphI and ligated with pHSG298 gxrA (Fujita, T. et al., Appl. Microbiol. Biothechnol. 97, 8887-8894 (2013)) that had already been treated with the same enzymes, to prepare pHSG298-AtPAL4.

(2) Preparation of pET28a-RgPAL

PAL derived from the yeast *Rhodotorula glutinis* (nucleotide sequence listed as SEQ ID NO: 1, amino acid sequence listed as SEQ ID NO: 2) was subjected to restriction enzyme treatment using NdeI and EcoRI, and then ligated with plasmid pET28a(Novagen) that had been subjected to restriction enzyme treatment using the same NdeI and EcoRI, to prepare pET28a-RgPAL.

(3) Preparation of pET28a-AtPAL4

PAL derived from the plant *Arabidopsis thaliana* was amplified by PCR using two primers (5'-CCCATATG-GAGCTATGCAATCAAAACAATC-3' and 5'-CCGAAT-TCTCAACAGATTGAAACCGGAGCTCCG-3'), and then subjected to restriction enzyme treatment using NdeI and EcoRI and ligated with the plasmid pET28a (Novagen) that had been subjected to restriction enzyme treatment using the same NdeI and EcoRI, to prepare pET28a-RgPAL.

REFERENCE EXAMPLE 1

Plant-Derived PAL with 4APAL Activity

Previous research has demonstrated that *Arabidopsis thaliana*-derived AtPAL4 exhibits high PAL activity. The present inventors therefore conjectured that AtPAL4 has not only high PAL activity but also high 4APAL activity, and measured the 4APAL activity of the AtPAL4 recombinant enzyme. A crude extract of a strain obtained by cloning the AtPAL4 gene to pHSG298 vector and introducing it into *Escherichia coli* NST37 (NST37-pHSG298-AtPAL4) exhibited 0.012 μmol/min/mg 4APAL activity as shown in Table 2.

TABLE 2

PAL and 4APAL activity of AtPAL4 in NST37(DE) host (μmol/min/mg)

| PAL activity | 0.18 |
|---|---|
| 4APAL activity | 0.012 |

Also, the IPTG concentration added during culturing of *Escherichia coli* NST37-pHSG298-AtPAL4 was investigated with varying inducing conditions. Upon investigation with addition of 0.01 mM, 0.1 mM, 1 mM and 2 mM IPTG, it was confirmed in SDS-PAGE that the AtPAL4 production level was high under all of the culturing conditions (data not shown). Thus, NST37-pHSG298-AtPAL4 was used for resting cell reaction, and the concentration of 4-aminocinnamic acid in the reaction mixture after 24 hours from the start of the reaction was measured and the production amount was quantified. As a result, the production of 4-aminocinnamic acid was maximum at 67 mg/L when using 2 mM IPTG.

REFERENCE EXAMPLE 2

Preparation of AtPAL4 Mutants

With the AtPAL4-transferred *Escherichia coli* NST37-pHSG298-AtPAL4, 4-aminophenylalanine was converted to 4-aminocinnamic acid in the resting cell reaction, but the production amount was a maximum of 67 mg/L, which was less than satisfactory. It was expected that the 4APAL activity would be insufficient for production with glucose as the starting material, where an even greater conversion rate is desired. It was attempted to further increase the 4APAL activity of AtPAL4 by modifying the amino acid sequence of AtPAL4. In Watts KT. et al. Discovery of a Substrate Selectivity Switch in Tyrosine Ammonia-Lyase, a Member of the Aromatic Amino Acid Lyase Family (2006) Chemistry & Biology, 13, 1317-1326, it is reported that by making a change from histidine to phenylalanine at an amino acid associated with substrate selectivity conserved in enzymes belonging to the aromatic amino acid lyase family (Tyrosine Ammonia Lyase derived from purple photosynthetic bacteria and PAL derived from cyanobacteria/corn/parsley/oleaginous yeast), the substrate specificity is changed from tyrosine to phenylalanine. When the amino acid sequences of enzymes belonging to the aromatic lyase family were compared with AtPAL4, and the relevant amino acid was identified, the amino acid was found to correspond to histidine at position 123 in AtPAL4 (H123). The difference between 4-aminophenylalanine as the substrate of the invention and phenylalanine as the original substrate of PAL is the presence or absence of the amino group at position 4. We therefore decided to replace H123 with glutamic acid or aspartic acid, as acidic amino acids expected to more easily participate in ionic bonding with amino groups. The *Escherichia coli* strains producing modified AtPAL4 (NST37-pHSG298-AtPAL4-H123D and NST37-pHSG298-AtPAL4-H123E) were cultured, resting cell reaction was conducted by the same method and the PAL activity and 4APAL activity were measured. As a result, as shown in FIG. 1, in resting cells the amount of cinnamic acid production decreased to 0.06-fold by introduction of the H123E mutation, while production of 4-aminophenylalanine increased to 1.25-fold (see FIG. 1(A)). This indicated that by mutating H123 to glutamic acid, the selectivity of AtPAL4 for 4aminophenylalanine is increased. Moreover, the results of activity measurement indicated that the 4APAL activity of AtPAL4-H123E-transferred *Escherichia coli* was 1.2 times the wild type activity (see FIG. 1(B)). It was conjectured that the increase in enzyme activity contributes to increase in productivity in the resting cell reaction.

REFERENCE EXAMPLE 3

Effect of pH on NST37-pHSG298-AtPAL4 Resting Cell Reaction

Figure 2:
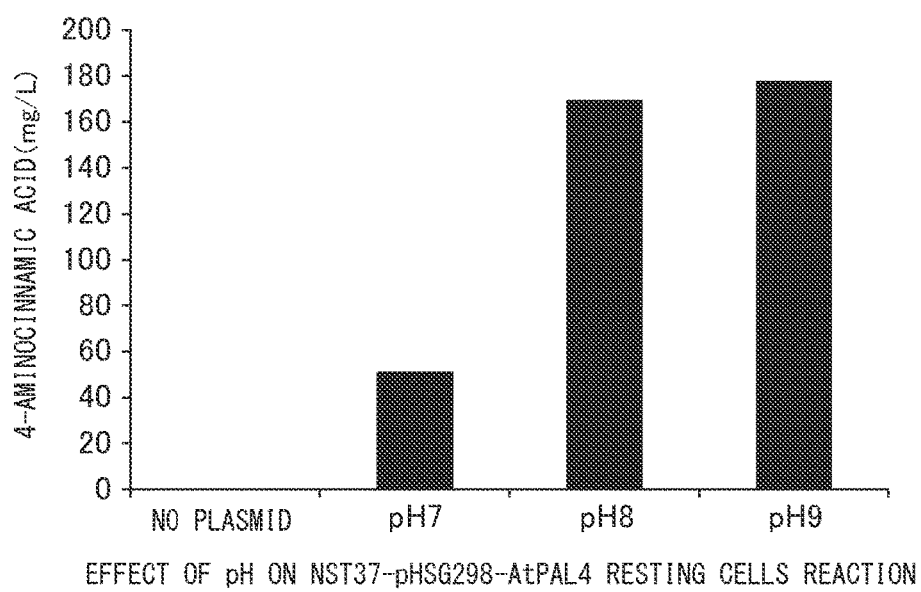
FIG. 2 is a graph showing the effect of pH on NST37-pHSG298-AtPAL4 resting cells reaction.

NST37-pHSG298-AtPAL4 resting cell reaction was conducted using reaction mixtures at pH 7, pH 8 and pH 9. As a control there was used *Escherichia coli* NST37 without plasmid transfer. First, comparison with the control confirmed that a peak for 4-aminocinnamic acid is notably detected only when the vector is present, and that reaction proceeds from 4-aminophenylalanine to 4-aminocinnamic acid by AtPAL4. As shown in FIG. 2, 4-aminocinnamic acid was only produced at 51.3 mg/L at pH 7, but when resting cells reaction was conducted at pH 8 and pH 9, 4-aminocinnamic acid was produced in the reaction mixture at 170 mg/L and 178 mg/L, respectively, thus demonstrating that 4-aminocinnamic acid is produced by resting cell reaction at pH 8 and pH 9.

EXAMPLE 1

Yeast-Derived PAL with PAL Activity

*Escherichia coli* BL21-pET28a-RgPAL was prepared by transferring a plasmid obtained by cloning PAL derived from the yeast *Rhodotorula glutinis* (hereunder also referred to as "RgPAL"), which is known to have PAL activity, in pET28a, into *Escherichia coli* BL21(DE3), and it was used to attempt production of 4-aminocinnamic acid.

Figure 3:
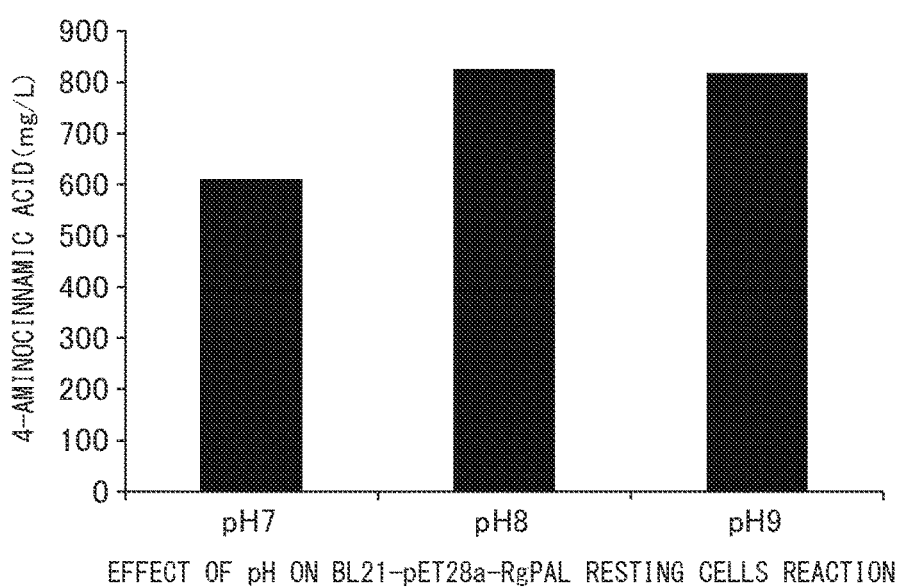
FIG. 3 is a graph showing the effect of pH on BL21-pET28a-RgPAL resting cells reaction.

The *Escherichia coli* BL21-pET28a-RgPAL cells were prepared by the following method. *Escherichia coli* BL21-pET28a-RgPAL was shake cultured overnight at 37° C., 120 rpm using medium containing 100 mg/L kanamycin sulfate in 5 ml of LB medium (1% tryptone, 0.5% yeast extract, 0.5% sodium chloride). A 2 mL portion of the obtained cell culture solution was transferred into 200 ml of the same medium in a 500 mL-volume Erlenmeyer flask, and then shake cultured at 37° C., 120 rpm. IPTG was added when the optical density of the culture reached 0.3, and shake culture was conducted at 28° C., 120 rpm for 12 hours. The obtained *Escherichia coli* BL21-pET28a-RgPAL cells were collected by centrifugal separation and rinsed once with 50 mM potassium phosphate (pH 7), after which they were suspended in the same buffer containing 20 mM of substrate (4-aminophenylalanine or phenylalanine), and incubated for 24 hours while shaking at 37° C. After the reaction, the produced 4-aminocinnamic acid or cinnamic acid was quantified using HPLC. Reaction was also carried out in aqueous 50 mM potassium phosphate at pH 8 or 9, using the same method as above. As a result, as shown in FIG. 3, the production amount of 4-aminocinnamic acid at pH 7 was 610 mg/L, while production of 4-aminocinnamic acid at pH 8 and pH 9 was 830 mg/L and 820 mg/L, respectively. Since higher conversion activity was exhibited when producing AtPAL4 at any pH, it was judged that RgPAL is a superior enzyme for production of 4-aminocinnamic acid. In particular, the conversion efficiency increased by 12-fold at pH 7.

EXAMPLE 2

Phenylalanine and 4-Aminophenylalanine Mixed Substrate

Figure 4:
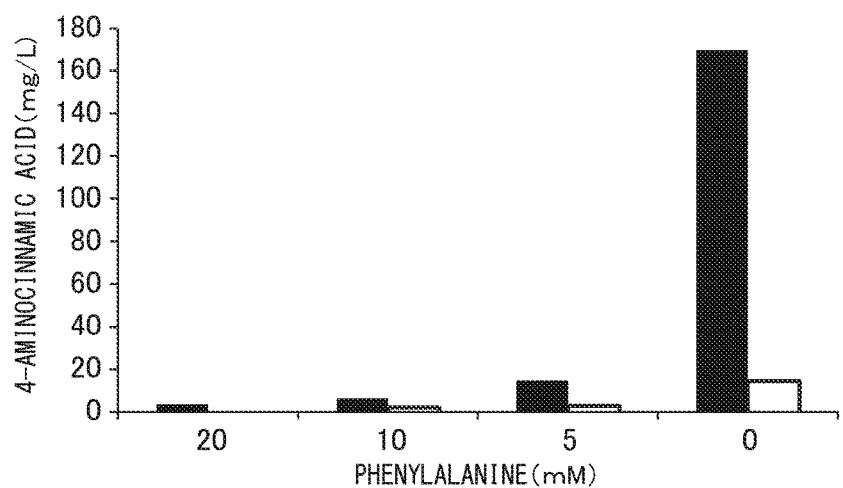
FIG. 4 is a pair of graphs showing production amounts of 4-aminocinnamic acid and cinnamic acid for a phenylalanine and 4-aminophenylalanine mixed substrate. (A): Production of 4-aminocinnamic acid; (B) production of cinnamic acid.
Figure 4:
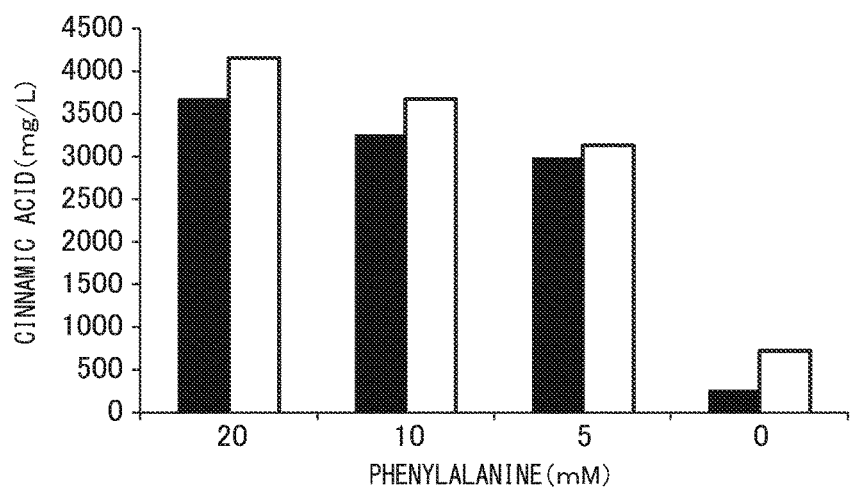

When producing 4-aminocinnamic acid from glucose, phenylalanine is produced as a by-product since phenylalanine-producing *Escherichia coli* is used. Therefore, the target PAL must be able to produce 4-aminophenylalanine under conditions in which phenylalanine is present. Thus, PAL activity by cells was measured under conditions with addition of a mixed substrate of phenylalanine and 4-aminophenylalanine. Specifically, as shown in FIG. 4, resting cell reaction was conducted with RgPAL-producing *Escherichia coli* BL21(DE3) or AtPAL4-producing *Escherichia coli* NST37, under conditions with the 4-aminophenylalanine concentration fixed at 20 mM and phenylalanine added thereto at 20 mM, 10 mM, 5 mM and 0 mM, and it was examined whether PAL reacts with 4-aminophenylalanine as its substrate even under conditions where phenylalanine is present, and if so, what its percentage of conversion is. As a result, when 4-aminophenylalanine alone was used as substrate, RgPAL produced more 4-aminocinnamic acid in an amount of 12 times compared to AtPAL4. In addition, when 4-aminophenylalanine alone was used as substrate, RgPAL only produced cinnamic acid at 36% compared to AtPAL4. Even when both phenylalanine and 4-aminophenylalanine were present, RgPAL produced more 4-aminocinnamic acid than AtPAL4, with a small amount of cinnamic acid. This demonstrated that RgPAL has higher specificity for 4-aminophenylalanine than AtPAL4.

EXAMPLE 3

Production Level of Recombinant Enzyme in Crude Cell Extract

The differences in 4APAL activity exhibited by *Escherichia coli* cells producing AtPAL4 and its mutants, obtained by transferring pET28a-AtPAL4 and its derivatives and pET28a-RgPAL into BL21(DE3), and RgPAL, are thought to be due to differences in PAL production level in each *Escherichia coli*, and therefore the production levels of RgPAL and AtPAL4 by *Escherichia coli* were examined. First, production was confirmed by SDS-PAGE. Assuming a molecular weight of 75.5 kDa for AtPAL4 and its mutants and a molecular weight of 75.6 kDa for RgPAL, bands corresponding to these were confirmed by SDS-PAGE in *Escherichia coli* in which each PAL had been transferred.

Figure 5:
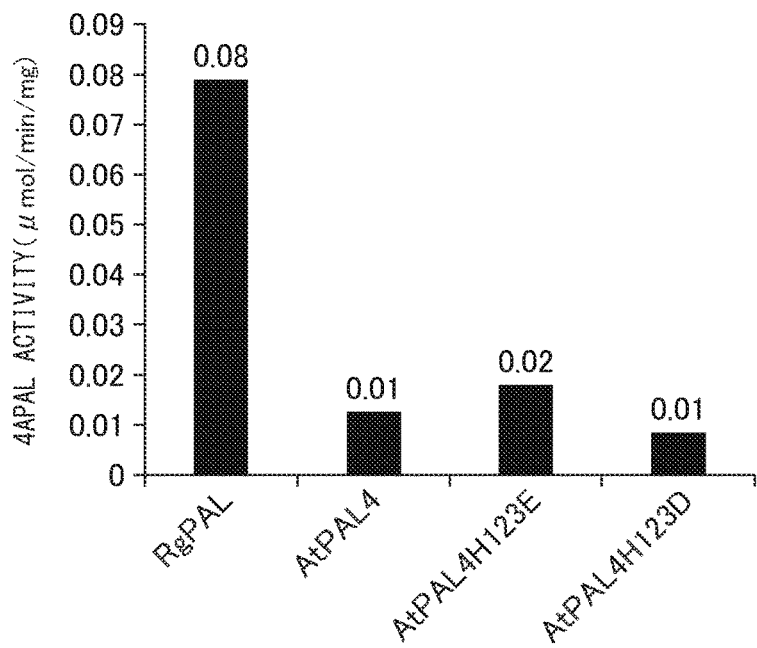
FIG. 5 is a pair of graphs showing 4APAL activity (A) and PAL activity (B) for each enzyme using crude cell extracts.
Figure 5:
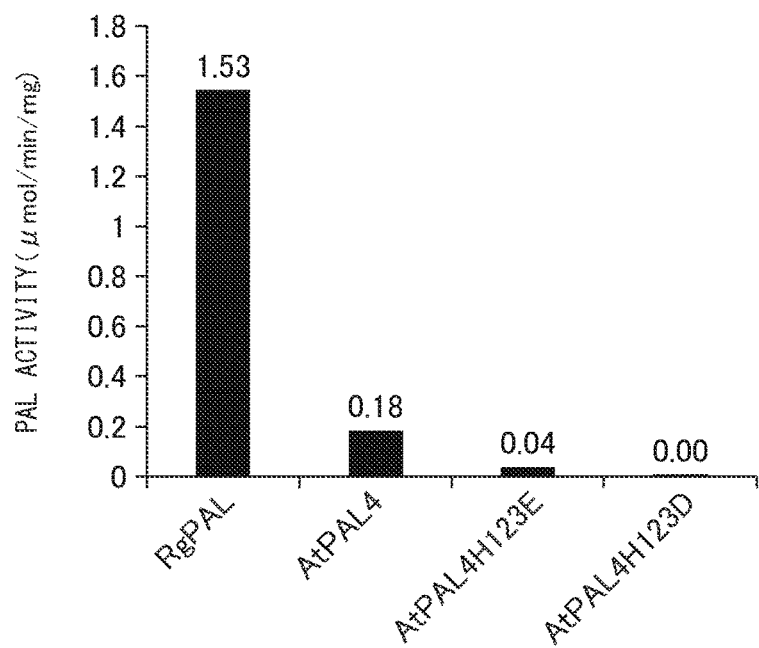

Also, as shown in FIG. 5, activity measurement was carried out using a crude cell extract, and the production levels of the enzymes were quantified. The concentration of 4-aminophenylalanine or 4-aminocinnamic acid used as the substrate was 20 mM. As a result, the crude cell extract of *Escherichia coli* producing RgPAL exhibited the highest levels of PAL activity and 4APAL activity. The PAL activity and 4APAL activity of RgPAL were 8.5-fold and 8-fold, respectively, compared to those of AtPAL4. These results suggested that one of the reasons for the high production of 4-aminocinnamic acid when RgPAL was produced in the resting cell reaction was due to the high production level of RgPAL.

EXAMPLE 4

Activity Measurement of Recombinant Purified Enzyme

Since pET28AtPAL4 and its mutants and RgPAL were produced as fusion proteins with His-tag in the *Escherichia coli* of Example 3, these enzymes could be easily purified using an affinity column. After culturing the producing cells, the cells were collected, disrupted and purified. The purified enzymes were used to calculate the $K_m$ values and $k_{cat}$ values. The results for the $K_m$ values and $k_{cat}$ values are shown in Tables 3 and 4, respectively.

TABLE 3

| Km value (mM) | AtPAL4 | AtPAL4H123E | AtPAL4H123D | RgPAL |
|---|---|---|---|---|
| Phenylalanine | 0.040 | 0.47 | 0.57 | 0.098 |
| 4-Aminophenylalanine | >40 | >40 | >40 | 22 |

TABLE 4

| Kcat value (s$^{-1}$) | AtPAL4 | AtPAL4H123E | AtPAL4H123D | RgPAL |
|---|---|---|---|---|
| Phenylalanine | 5.1 | 6.5 | 0.72 | 3.4 |
| 4-Aminophenylalanine | >0.40 | >0.40 | >0.40 | 0.44 |

As shown in Table 3, the K$_m$ values for phenylalanine were 1.0 mM or lower in all cases except for AtPAL4H123D, with RgPAL together with AtPAL4 being the lowest at ≤0.1 mM. Also, the K$_m$ value for 4-aminophenylalanine was lowest with RgPAL, at 22 mM. The purified enzyme activity was highest with RgPAL, for both PAL activity and 4APAL activity. Furthermore, as shown in Table 4, the k$_{cat}$ values for 4-aminophenylalanine were equivalent with RgPAL and AtPAL4 and its modified form, thus suggesting that RgPAL exhibits high conversion activity due to high affinity for 4-aminophenylalanine.

EXAMPLE 5

Extraction of 4-Aminocinnamic Acid

Figure 6:
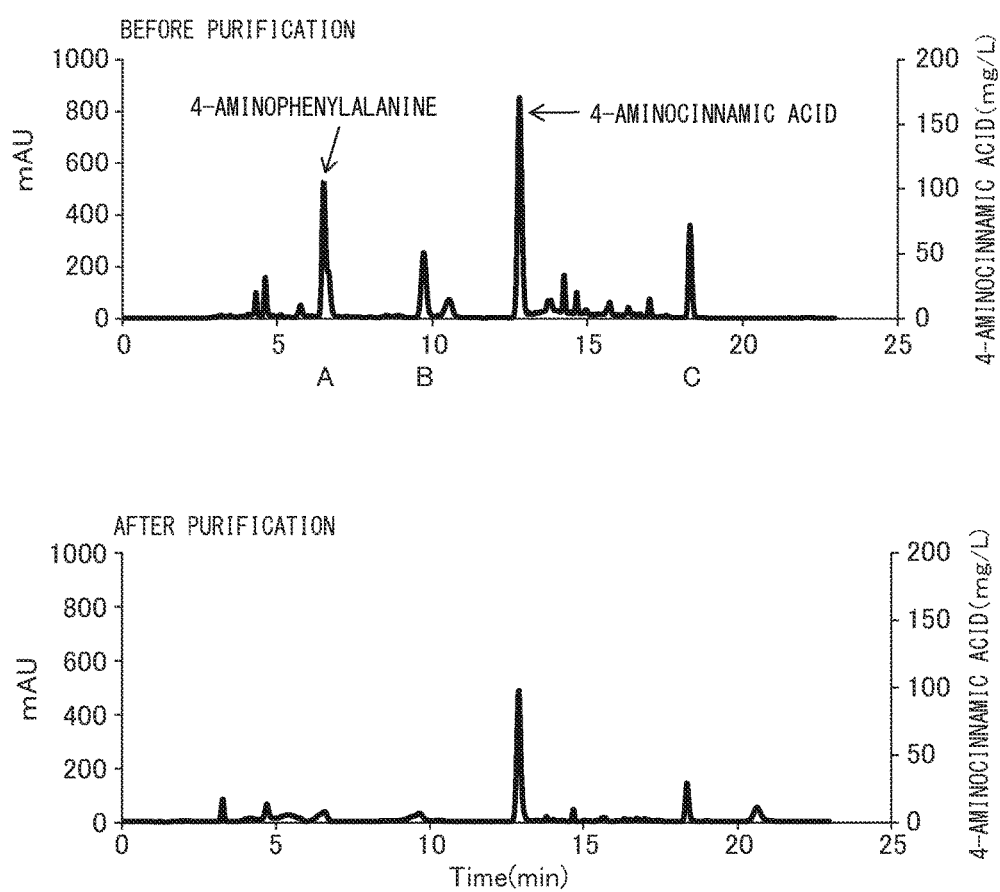
FIG. 6 is a pair of graphs showing the results for HPLC analysis of 4-aminocinnamic acid extraction from a resting cells reaction solution.

It was attempted to extract 4-aminocinnamic acid from the reaction mixture after resting cell reaction. First, a 20 ml portion of the supernatant obtained by removing the cells from the reaction mixture was collected and the water was vaporized off with an evaporator. Next, since 4-aminocinnamic acid is soluble in acetone, 5 ml of acetone was added to the obtained solid to extract the 4-aminocinnamic acid, after which the acetone was evaporated off in an attempt to collect the 4-aminocinnamic acid. FIG. 6 shows the results of HPLC analysis of the obtained extract. The heights of the three major peaks A, B and C other than 4-aminocinnamic acid were successfully reduced by 93%, 89% and 61%, respectively. This resulted in a purity of ≥90%. The yield of 4-aminocinnamic acid was 58%, as the purity where the consumed 4-APhe was defined as 100.

INDUSTRIAL APPLICABILITY

Since the enzyme of the invention has higher enzyme activity than *Arabidopsis thaliana*-derived ammonia lyase, reaching 4-aminocinnamic acid production of about 1 g/L, the enzyme can be used in a method allowing industrial mass production of 4-aminocinnamic acid from 4-aminophenylalanine.

[Sequence Listing]

What is claimed is:

1. A method for producing 4-aminocinnamic acid, comprising the step of converting 4-aminophenylalanine to 4-aminocinnamic acid with phenylalanine ammonia lyase derived from yeast *Rhodotorula glutinis*, or a modified form thereof, wherein the modified form has the amino acid sequence of phenylalanine ammonia lyase derived from the yeast *Rhodotorula glutinis*, with a deletion, substitution, insertion or addition of one to ten amino acids, and has 4-aminocinnamic acid synthesis activity.

2. A method for producing 4-aminocinnamic acid, comprising the step of converting 4-aminophenylalanine to 4-aminocinnamic acid with an enzyme, wherein the enzyme selected from the group consisting of:
   (a) proteins comprising the amino acid sequence of SEQ ID NO: 2;
   (b) proteins comprising an amino acid sequence having at least 95% sequence identity with the amino acid sequence of SEQ ID NO: 2, and having 4-aminocinnamic acid synthesis activity;
   (c) proteins comprising the amino acid sequence of SEQ ID NO: 2 with a deletion, substitution, insertion or addition of one to ten amino acids, and having 4-aminocinnamic acid synthesis activity; and
   (d) proteins encoded by nucleic acids comprising a nucleotide sequence that hybridizes with a nucleic acid comprising a nucleotide sequence that is complementary with a nucleotide sequence coding for the amino acid sequence of SEQ ID NO: 2, under highly stringent conditions, and that codes for a protein having 4-aminocinnamic acid synthesis activity.

3. The method according to claim 2, which comprises culturing or reacting resting cells of a microbe that produces the enzyme in a solution.

4. The method according to claim 3, wherein the microbe is Escherichia coli.

5. The method according to claim 3, wherein the resting cell reaction is conducted at pH 8 to pH 9.

6. The method according to claim 3, wherein the resting cells are selected from the group consisting of cultured cells, powdered cells and immobilized cells.

7. The method according to claim 1, wherein the modified form has the amino acid sequence of phenylalanine ammonia lyase derived from the yeast *Rhodotorula glutinis*, with a deletion, substitution, insertion or addition of one to five amino acids, and has 4-aminocinnamic acid synthesis activity.

8. The method according to claim 1, wherein the modified form has the amino acid sequence of phenylalanine ammonia lyase derived from the yeast *Rhodotorula glutinis*, with a deletion, substitution, insertion or addition of one to three amino acids, and has 4-aminocinnamic acid synthesis activity.

9. The method according to claim 2, wherein the enzyme is a protein comprising an amino acid sequence having at least 98% sequence identity with the amino acid sequence listed as SEQ ID NO: 2, and has 4-aminocinnamic acid synthesis activity.

10. The method according to claim 2, wherein the enzyme is a protein comprising an amino acid sequence having at least 99% sequence identity with the amino acid sequence listed as SEQ ID NO: 2, and has 4-aminocinnamic acid synthesis activity.

11. The method according to claim 2, wherein the enzyme is a protein comprising the amino acid sequence listed as SEQ ID NO: 2 with a deletion, substitution, insertion or addition of one to five amino acids, and has 4-aminocinnamic acid synthesis activity.

12. The method according to claim 2, wherein the enzyme is a protein comprising the amino acid sequence listed as SEQ ID NO: 2 with a deletion, substitution, insertion or addition of one to three amino acids, and has 4-aminocinnamic acid synthesis activity.

* * * * *

```
SEQUENCE LISTING

<160> NUMBER OF SEQ ID NOS: 4

<210> SEQ ID NO 1
<211> LENGTH: 2121
<212> TYPE: DNA
<213> ORGANISM: Artificial Sequence
<220> FEATURE:
<221> NAME/KEY: CDS
<222> LOCATION: (1)..(2121)
<223> OTHER INFORMATION: RgPAL cDNA

<400> SEQUENCE: 1 atg gcc ccc tcc gtc gac tcg atc gcg act tcg gtc gcc aac tcg ctc      48
Met Ala Pro Ser Val Asp Ser Ile Ala Thr Ser Val Ala Asn Ser Leu
1               5                   10                  15 tcg aac gga ctc gcc ggc gac ctc cgc aag aag act tcg ggt gct ggc      96
Ser Asn Gly Leu Ala Gly Asp Leu Arg Lys Lys Thr Ser Gly Ala Gly
            20                  25                  30 tcc ctg ctg ccg acc acc gag act acc cag atc gac atc gtc gag cgc     144
Ser Leu Leu Pro Thr Thr Glu Thr Thr Gln Ile Asp Ile Val Glu Arg
        35                  40                  45 atc ttg gcc gac gcc ggc gcg acg gac cag atc aaa ctc gac ggg tat     192
Ile Leu Ala Asp Ala Gly Ala Thr Asp Gln Ile Lys Leu Asp Gly Tyr
    50                  55                  60 acc ctc acc ctc ggc gac gtc gtc ggc gcc gcc cgc cgc ggc cgc acc     240
Thr Leu Thr Leu Gly Asp Val Val Gly Ala Ala Arg Arg Gly Arg Thr
65                  70                  75                  80 gtc aag gtc gcc gat agc ccc cag att cgc gag aag atc gat gcc agt     288
Val Lys Val Ala Asp Ser Pro Gln Ile Arg Glu Lys Ile Asp Ala Ser
                85                  90                  95 gtc gag ttc ctc cgc acc cag ctt gac aac agt gtc tac ggt gtc acg     336
Val Glu Phe Leu Arg Thr Gln Leu Asp Asn Ser Val Tyr Gly Val Thr
            100                 105                 110 acc ggc ttc ggc ggc tcg gca gac acc cgg acg gag gac gcg atc tcg     384
Thr Gly Phe Gly Gly Ser Ala Asp Thr Arg Thr Glu Asp Ala Ile Ser
        115                 120                 125
```

```
ctg cag aag gct ctg ctc gag cac caa ctc tgc ggt gtc ctg ccc acc      432
Leu Gln Lys Ala Leu Leu Glu His Gln Leu Cys Gly Val Leu Pro Thr
    130             135                 140 tcg atg gac ggg ttc gcg ctc gga cgt ggc ctc gag aac tcg ctc ccg      480
Ser Met Asp Gly Phe Ala Leu Gly Arg Gly Leu Glu Asn Ser Leu Pro
145                 150                 155                 160 ctc gag gtt gtt cgt ggc gcg atg acg atc cgt gtc aac tcg ctc acg      528
Leu Glu Val Val Arg Gly Ala Met Thr Ile Arg Val Asn Ser Leu Thr
                165                 170                 175 cgc ggc cac tcg gcg gtc cgc atc gtc gtc ctc gaa gcc ctc acc aac      576
Arg Gly His Ser Ala Val Arg Ile Val Val Leu Glu Ala Leu Thr Asn
                180                 185                 190 ttc ctc aac cac ggc atc acc ccg atc gtc ccc ctc cgc ggc acc atc      624
Phe Leu Asn His Gly Ile Thr Pro Ile Val Pro Leu Arg Gly Thr Ile
            195                 200                 205 tcg gca tcg ggt gac ctt tcc ccc ctc tcg tac atc gcc gcc tcg atc      672
Ser Ala Ser Gly Asp Leu Ser Pro Leu Ser Tyr Ile Ala Ala Ser Ile
    210                 215                 220 acc ggt cac cca gac tcg aag gtg cac gtc gac ggc caa atc atg tcc      720
Thr Gly His Pro Asp Ser Lys Val His Val Asp Gly Gln Ile Met Ser
225                 230                 235                 240 gcc cag gag gcg atc gct ctc aag ggt ctc caa cct gtc gtc ctc ggt      768
Ala Gln Glu Ala Ile Ala Leu Lys Gly Leu Gln Pro Val Val Leu Gly
                245                 250                 255 ccg aag gag ggt ctc ggg ctc gtc aac ggc acc gcc gtc tcc gcg tcc      816
Pro Lys Glu Gly Leu Gly Leu Val Asn Gly Thr Ala Val Ser Ala Ser
                260                 265                 270 atg gcc act ctc gcc ctc acc gac gcg cat gtc ctc tcg ttg ctc gcc      864
Met Ala Thr Leu Ala Leu Thr Asp Ala His Val Leu Ser Leu Leu Ala
            275                 280                 285 cag gcc aac acg gcc ctg acc gtc gag gcc atg gtc gga cac gcc ggc      912
Gln Ala Asn Thr Ala Leu Thr Val Glu Ala Met Val Gly His Ala Gly
    290                 295                 300 tcg ttc cac ccg ttc ctg cac gat gtc act cgc ccg cac ccg acc cag      960
Ser Phe His Pro Phe Leu His Asp Val Thr Arg Pro His Pro Thr Gln
305                 310                 315                 320 atc gag gtc gcg cgc aac att agg acg ctc ctc gag ggc agc aag tac     1008
Ile Glu Val Ala Arg Asn Ile Arg Thr Leu Leu Glu Gly Ser Lys Tyr
                325                 330                 335 gcc gtc cac cat gag acc gag gtc aag gtc aag gac gac gag ggc atc     1056
Ala Val His His Glu Thr Glu Val Lys Val Lys Asp Asp Glu Gly Ile
                340                 345                 350 ctc cgg cag gac cga tac ccg ctc cgc tgc tcg ccc cag tgg ctc ggg     1104
Leu Arg Gln Asp Arg Tyr Pro Leu Arg Cys Ser Pro Gln Trp Leu Gly
            355                 360                 365 cct ctt gtc agt gac atg atc cac gcc cac tcg gtc ctc tcc ctc gag     1152
Pro Leu Val Ser Asp Met Ile His Ala His Ser Val Leu Ser Leu Glu
    370                 375                 380 gcg ggt cag tcg acc acc gac aac ccc ctg atc gac ctc gag aac aag     1200
Ala Gly Gln Ser Thr Thr Asp Asn Pro Leu Ile Asp Leu Glu Asn Lys
385                 390                 395                 400 atg acc cac cac ggt ggc gcc ttc atg gcg agc agc gtc ggt aac acc     1248
Met Thr His His Gly Gly Ala Phe Met Ala Ser Ser Val Gly Asn Thr
                405                 410                 415 atg gag aag act cgt ctc gcc gtc gca ctt atg ggc aag gtt agc ttc     1296
Met Glu Lys Thr Arg Leu Ala Val Ala Leu Met Gly Lys Val Ser Phe
                420                 425                 430 act cag ctc acc gag atg ctc aac gcc ggc atg aac cgc gcg ctt ccc     1344
Thr Gln Leu Thr Glu Met Leu Asn Ala Gly Met Asn Arg Ala Leu Pro
            435                 440                 445
```

```
tcc tgc ctc gcc gcc gag gac ccg tct ctg tcc tac cac tgc aag ggt    1392
Ser Cys Leu Ala Ala Glu Asp Pro Ser Leu Ser Tyr His Cys Lys Gly
450                 455                 460 ctc gac atc gcc gcc gct gca tac act tcg gag ctc ggt cac ctc gcg    1440
Leu Asp Ile Ala Ala Ala Ala Tyr Thr Ser Glu Leu Gly His Leu Ala
465                 470                 475                 480 aac cca gtc tcg acc cac gtt cag ccg gca gag atg ggc aat cag gcg    1488
Asn Pro Val Ser Thr His Val Gln Pro Ala Glu Met Gly Asn Gln Ala
            485                 490                 495 atc aac tcg ctc gcc ctc atc tcg gcc cgt cgc acc gcc gag gcg aac    1536
Ile Asn Ser Leu Ala Leu Ile Ser Ala Arg Arg Thr Ala Glu Ala Asn
        500                 505                 510 gac gtc ctc tcg ctc ctc ctc gcc acc cac ctc tac tgc gtc ttg cag    1584
Asp Val Leu Ser Leu Leu Leu Ala Thr His Leu Tyr Cys Val Leu Gln
    515                 520                 525 gcg gtc gac ctg cgc gcg atg gag ttc gag cac acg aaa gag ttt gag    1632
Ala Val Asp Leu Arg Ala Met Glu Phe Glu His Thr Lys Glu Phe Glu
530                 535                 540 ccg atg gtc acc gac ttg ctc aag cag cac ttt ggc gcg ctc gcg aca    1680
Pro Met Val Thr Asp Leu Leu Lys Gln His Phe Gly Ala Leu Ala Thr
545                 550                 555                 560 gcc gac gtc gag gac aag gtc cgc aaa tcg atc tac aag cgg ctg cag    1728
Ala Asp Val Glu Asp Lys Val Arg Lys Ser Ile Tyr Lys Arg Leu Gln
            565                 570                 575 cag aac aac tcg tac gac ctc gag cag cgg tgg cac gac acg ttc tcg    1776
Gln Asn Asn Ser Tyr Asp Leu Glu Gln Arg Trp His Asp Thr Phe Ser
        580                 585                 590 gtc gcg acc ggc gcc gtc gtc gaa gcc ctc gcc ggg aac gag gtg tcg    1824
Val Ala Thr Gly Ala Val Val Glu Ala Leu Ala Gly Asn Glu Val Ser
    595                 600                 605 ctc gcg agc ctg aac gcc tgg aag gtc gcg tgc gct gag aag gcc atc    1872
Leu Ala Ser Leu Asn Ala Trp Lys Val Ala Cys Ala Glu Lys Ala Ile
610                 615                 620 gcc ctg acc cgc acc gtg cgc gac tcg ttc tgg gcc gcg ccg tcg tcg    1920
Ala Leu Thr Arg Thr Val Arg Asp Ser Phe Trp Ala Ala Pro Ser Ser
625                 630                 635                 640 gcg tcg ccc gcg ctc aag tac ctc tcg ccg cgg act cgc atc ctg tac    1968
Ala Ser Pro Ala Leu Lys Tyr Leu Ser Pro Arg Thr Arg Ile Leu Tyr
            645                 650                 655 tcg ttc gtc cgg gaa gac gtc ggc gtc aag gcc cgc cgc ggc gac gtc    2016
Ser Phe Val Arg Glu Asp Val Gly Val Lys Ala Arg Arg Gly Asp Val
        660                 665                 670 tac ctc ggc aag cag gag gtc acg atc ggg acc aac gtc agc cgc atc    2064
Tyr Leu Gly Lys Gln Glu Val Thr Ile Gly Thr Asn Val Ser Arg Ile
    675                 680                 685 tac gag gcg atc aag gac ggc cgc att gct ccg gtc ctc gtc aag atg    2112
Tyr Glu Ala Ile Lys Asp Gly Arg Ile Ala Pro Val Leu Val Lys Met
690                 695                 700 atg gca taa                                                        2121
Met Ala
705

<210> SEQ ID NO 2
<211> LENGTH: 706
<212> TYPE: PRT
<213> ORGANISM: Artificial Sequence
<220> FEATURE:
<223> OTHER INFORMATION: RgPAL cDNA
```

```
<400> SEQUENCE: 2

Met Ala Pro Ser Val Asp Ser Ile Ala Thr Ser Val Ala Asn Ser Leu
1               5                   10                  15

Ser Asn Gly Leu Ala Gly Asp Leu Arg Lys Thr Ser Gly Ala Gly
            20                  25                  30

Ser Leu Leu Pro Thr Thr Glu Thr Gln Ile Asp Ile Val Glu Arg
            35              40                  45

Ile Leu Ala Asp Ala Gly Ala Thr Asp Gln Ile Lys Leu Asp Gly Tyr
    50                  55                  60

Thr Leu Thr Leu Gly Asp Val Gly Ala Ala Arg Arg Gly Arg Thr
65              70                  75                  80

Val Lys Val Ala Asp Ser Pro Gln Ile Arg Glu Lys Ile Asp Ala Ser
                85                  90                  95

Val Glu Phe Leu Arg Thr Gln Leu Asp Asn Ser Val Tyr Gly Val Thr
                100                 105                 110

Thr Gly Phe Gly Gly Ser Ala Asp Thr Arg Thr Glu Asp Ala Ile Ser
            115                 120                 125

Leu Gln Lys Ala Leu Leu Glu His Gln Leu Cys Gly Val Leu Pro Thr
130                 135                 140

Ser Met Asp Gly Phe Ala Leu Gly Arg Gly Leu Glu Asn Ser Leu Pro
145                 150                 155                 160

Leu Glu Val Val Arg Gly Ala Met Thr Ile Arg Val Asn Ser Leu Thr
                165                 170                 175

Arg Gly His Ser Ala Val Arg Ile Val Val Leu Glu Ala Leu Thr Asn
            180                 185                 190

Phe Leu Asn His Gly Ile Thr Pro Ile Val Pro Leu Arg Gly Thr Ile
        195                 200                 205

Ser Ala Ser Gly Asp Leu Ser Pro Leu Ser Tyr Ile Ala Ala Ser Ile
210                 215                 220

Thr Gly His Pro Asp Ser Lys Val His Val Asp Gly Gln Ile Met Ser
225                 230                 235                 240

Ala Gln Glu Ala Ile Ala Leu Lys Gly Leu Gln Pro Val Val Leu Gly
                245                 250                 255

Pro Lys Glu Gly Leu Gly Leu Val Asn Gly Thr Ala Val Ser Ala Ser
            260                 265                 270

Met Ala Thr Leu Ala Leu Thr Asp Ala His Val Leu Ser Leu Leu Ala
            275                 280                 285

Gln Ala Asn Thr Ala Leu Thr Val Glu Ala Met Val Gly His Ala Gly
        290                 295                 300

Ser Phe His Pro Phe Leu His Asp Val Thr Arg Pro His Pro Thr Gln
305                 310                 315                 320

Ile Glu Val Ala Arg Asn Ile Arg Thr Leu Leu Glu Gly Ser Lys Tyr
                325                 330                 335

Ala Val His His Glu Thr Glu Val Lys Val Lys Asp Asp Glu Gly Ile
            340                 345                 350

Leu Arg Gln Asp Arg Tyr Pro Leu Arg Cys Ser Pro Gln Trp Leu Gly
        355                 360                 365

Pro Leu Val Ser Asp Met Ile His Ala His Ser Val Leu Ser Leu Glu
370                 375                 380

Ala Gly Gln Ser Thr Thr Asp Asn Pro Leu Ile Asp Leu Glu Asn Lys
385                 390                 395                 400

Met Thr His His Gly Gly Ala Phe Met Ala Ser Ser Val Gly Asn Thr
                405                 410                 415
```

-continued

```
Met Glu Lys Thr Arg Leu Ala Val Ala Leu Met Gly Lys Val Ser Phe
            420                 425                 430

Thr Gln Leu Thr Glu Met Leu Asn Ala Gly Met Asn Arg Ala Leu Pro
        435                 440                 445

Ser Cys Leu Ala Ala Glu Asp Pro Ser Leu Ser Tyr His Cys Lys Gly
    450                 455                 460

Leu Asp Ile Ala Ala Ala Ala Tyr Thr Ser Glu Leu Gly His Leu Ala
465                 470                 475                 480

Asn Pro Val Ser Thr His Val Gln Pro Ala Glu Met Gly Asn Gln Ala
                485                 490                 495

Ile Asn Ser Leu Ala Leu Ile Ser Ala Arg Arg Thr Ala Glu Ala Asn
            500                 505                 510

Asp Val Leu Ser Leu Leu Leu Ala Thr His Leu Tyr Cys Val Leu Gln
        515                 520                 525

Ala Val Asp Leu Arg Ala Met Glu Phe Glu His Thr Lys Glu Phe Glu
    530                 535                 540

Pro Met Val Thr Asp Leu Leu Lys Gln His Phe Gly Ala Leu Ala Thr
545                 550                 555                 560

Ala Asp Val Glu Asp Lys Val Arg Lys Ser Ile Tyr Lys Arg Leu Gln
                565                 570                 575

Gln Asn Asn Ser Tyr Asp Leu Glu Gln Arg Trp His Asp Thr Phe Ser
            580                 585                 590

Val Ala Thr Gly Ala Val Val Glu Ala Leu Ala Gly Asn Glu Val Ser
        595                 600                 605

Leu Ala Ser Leu Asn Ala Trp Lys Val Ala Cys Ala Glu Lys Ala Ile
    610                 615                 620

Ala Leu Thr Arg Thr Val Arg Asp Ser Phe Trp Ala Ala Pro Ser Ser
625                 630                 635                 640

Ala Ser Pro Ala Leu Lys Tyr Leu Ser Pro Arg Thr Arg Ile Leu Tyr
                645                 650                 655

Ser Phe Val Arg Glu Asp Val Gly Val Lys Ala Arg Arg Gly Asp Val
            660                 665                 670

Tyr Leu Gly Lys Gln Glu Val Thr Ile Gly Thr Asn Val Ser Arg Ile
        675                 680                 685

Tyr Glu Ala Ile Lys Asp Gly Arg Ile Ala Pro Val Leu Val Lys Met
    690                 695                 700

Met Ala
705
```

<210> SEQ ID NO 3
<211> LENGTH: 2124
<212> TYPE: DNA
<213> ORGANISM: Artificial Sequence
<220> FEATURE:
<221> NAME/KEY: CDS
<222> LOCATION: (1)..(2124)
<223> OTHER INFORMATION: AtPA4L cDNA

<400> SEQUENCE: 3

```
atg gag cta tgc aat caa aac aat cac atc acc gcc gtc tcg ggc gat      48
Met Glu Leu Cys Asn Gln Asn Asn His Ile Thr Ala Val Ser Gly Asp
1               5                   10                  15 ccg ttg aac tgg aac gcg acg gcc gaa gct ttg aaa ggg agc cac ctg      96
Pro Leu Asn Trp Asn Ala Thr Ala Glu Ala Leu Lys Gly Ser His Leu
            20                  25                  30
```

```
gat gag gtg aaa cga atg gtg aaa gag tat agg aaa gag gcg gtg aag       144
Asp Glu Val Lys Arg Met Val Lys Glu Tyr Arg Lys Glu Ala Val Lys
         35                  40                  45 tta gga ggt gag act ttg acg att ggt caa gta gcc gcc gtg gct aga       192
Leu Gly Gly Glu Thr Leu Thr Ile Gly Gln Val Ala Ala Val Ala Arg
 50                  55                  60 gga gga gga gga tct acg gtg gag cta gcg gag gag gct cgt gcc gga       240
Gly Gly Gly Gly Ser Thr Val Glu Leu Ala Glu Glu Ala Arg Ala Gly
 65                  70                  75                  80 gtc aag gcg agt agc gaa tgg gtg atg gag agc atg aac cga gga acg       288
Val Lys Ala Ser Ser Glu Trp Val Met Glu Ser Met Asn Arg Gly Thr
                 85                  90                  95 gac agt tat gga gtt acc aca ggg ttt ggt gca act tcc cat aga aga       336
Asp Ser Tyr Gly Val Thr Thr Gly Phe Gly Ala Thr Ser His Arg Arg
                100                 105                 110 acc aaa caa ggc ggt gca ctt caa aat gag ctt att agg ttc ttg aat       384
Thr Lys Gln Gly Gly Ala Leu Gln Asn Glu Leu Ile Arg Phe Leu Asn
            115                 120                 125 gcc gga ata ttt ggc ccc ggc gcc ggg gac acg tca cac acg ttg cca       432
Ala Gly Ile Phe Gly Pro Gly Ala Gly Asp Thr Ser His Thr Leu Pro
130                 135                 140 aag ccg aca aca aga gcg gca atg ctc gtc cgt gtc aac act ctc ctc       480
Lys Pro Thr Thr Arg Ala Ala Met Leu Val Arg Val Asn Thr Leu Leu
145                 150                 155                 160 caa ggc tac tcc ggt ata cgc ttc gag att ctc gaa gca att aca aag       528
Gln Gly Tyr Ser Gly Ile Arg Phe Glu Ile Leu Glu Ala Ile Thr Lys
                165                 170                 175 ctt ctc aac cac gaa atc act ccg tgc ctc cct ctc cgt ggc acc atc       576
Leu Leu Asn His Glu Ile Thr Pro Cys Leu Pro Leu Arg Gly Thr Ile
                180                 185                 190 acc gcc tcc ggt gac ctt gtt cct ctc tct tac atc gcc gga ctt ctc       624
Thr Ala Ser Gly Asp Leu Val Pro Leu Ser Tyr Ile Ala Gly Leu Leu
            195                 200                 205 act ggc cgt ccc aac tcc aaa gcc gtg ggt ccc tct ggt gag act ctc       672
Thr Gly Arg Pro Asn Ser Lys Ala Val Gly Pro Ser Gly Glu Thr Leu
        210                 215                 220 act gcc tct gag gcc ttt aag ctc gcc gga gta tcg tcc ttt ttc gag       720
Thr Ala Ser Glu Ala Phe Lys Leu Ala Gly Val Ser Ser Phe Phe Glu
225                 230                 235                 240 ctg cag cct aag gaa gga cta gca ctt gtg aac ggg aca gcg gtt gga       768
Leu Gln Pro Lys Glu Gly Leu Ala Leu Val Asn Gly Thr Ala Val Gly
                245                 250                 255 tcg ggt ttg gcc tca acg gtt ttg ttc gat gca aat att ttg gct gtt       816
Ser Gly Leu Ala Ser Thr Val Leu Phe Asp Ala Asn Ile Leu Ala Val
                260                 265                 270 tta tcg gaa gtt atg tct gcc atg ttc gca gag gtt atg caa ggg aaa       864
Leu Ser Glu Val Met Ser Ala Met Phe Ala Glu Val Met Gln Gly Lys
            275                 280                 285 ccg gag ttt aca gat cat ctt acg cat aag ctc aag cac cat ccc ggt       912
Pro Glu Phe Thr Asp His Leu Thr His Lys Leu Lys His His Pro Gly
        290                 295                 300 cag atc gaa gcc gcc gca att atg gaa cat ata tta gac gga agc tct       960
Gln Ile Glu Ala Ala Ala Ile Met Glu His Ile Leu Asp Gly Ser Ser
305                 310                 315                 320 tac gtt aaa gaa gct caa ctt ctc cac gaa atg gat cct ctt caa aaa      1008
Tyr Val Lys Glu Ala Gln Leu Leu His Glu Met Asp Pro Leu Gln Lys
                325                 330                 335 cct aaa caa gat cgg tac gct tta cgt acg tca cca caa tgg ctt ggg      1056
Pro Lys Gln Asp Arg Tyr Ala Leu Arg Thr Ser Pro Gln Trp Leu Gly
                340                 345                 350
```

-continued

```
ccg cag att gaa gtg atc aga gcg gct act aaa atg att gag cgt gag      1104
Pro Gln Ile Glu Val Ile Arg Ala Ala Thr Lys Met Ile Glu Arg Glu
        355                 360                 365 atc aac tct gtt aat gat aac cct ttg ata gat gtg tcg agg aac aag      1152
Ile Asn Ser Val Asn Asp Asn Pro Leu Ile Asp Val Ser Arg Asn Lys
    370                 375                 380 gcg ttg cac ggt gga aat ttc caa ggg aca ccg atc ggt gtt gcc atg      1200
Ala Leu His Gly Gly Asn Phe Gln Gly Thr Pro Ile Gly Val Ala Met
385                 390                 395                 400 gat aat tcc cgt cta gcc att gct tcc att ggg aaa ctc atg ttt gcg      1248
Asp Asn Ser Arg Leu Ala Ile Ala Ser Ile Gly Lys Leu Met Phe Ala
                405                 410                 415 cag ttt tct gaa cta gtg aac gat ttc tac aac aat ggt ttg cct tct      1296
Gln Phe Ser Glu Leu Val Asn Asp Phe Tyr Asn Asn Gly Leu Pro Ser
            420                 425                 430 aat cta tct ggt ggg aga aac cct agt ctt gat tac ggg ttt aaa ggc      1344
Asn Leu Ser Gly Gly Arg Asn Pro Ser Leu Asp Tyr Gly Phe Lys Gly
        435                 440                 445 gcg gaa ata gcc atg gct tct tat tgc tcc gag ctt cag ttc ctg gct      1392
Ala Glu Ile Ala Met Ala Ser Tyr Cys Ser Glu Leu Gln Phe Leu Ala
    450                 455                 460 aat ccc gtg acc aac cat gtc caa agc gca gag cag cat aac caa gac      1440
Asn Pro Val Thr Asn His Val Gln Ser Ala Glu Gln His Asn Gln Asp
465                 470                 475                 480 gtt aat tcc cta ggg cta atc tct agc agg aaa act gca gaa gca gtg      1488
Val Asn Ser Leu Gly Leu Ile Ser Ser Arg Lys Thr Ala Glu Ala Val
                485                 490                 495 gat atc ctc aag cta atg tcc aca acc tac tta gtc gcg ctt tgc caa      1536
Asp Ile Leu Lys Leu Met Ser Thr Thr Tyr Leu Val Ala Leu Cys Gln
            500                 505                 510 gcc gtt gat cta aga cat ctt gaa gag aat ctg aag aag gcg gtt aaa      1584
Ala Val Asp Leu Arg His Leu Glu Glu Asn Leu Lys Lys Ala Val Lys
        515                 520                 525 tca gca gtg agt cag gtg gcg aaa cgg gtc tta acc gtt ggt gcc aac      1632
Ser Ala Val Ser Gln Val Ala Lys Arg Val Leu Thr Val Gly Ala Asn
    530                 535                 540 ggg gag cta cat ccg tca agg ttc aca gaa cgt gat gtc ctc caa gtg      1680
Gly Glu Leu His Pro Ser Arg Phe Thr Glu Arg Asp Val Leu Gln Val
545                 550                 555                 560 gtt gac cga gag tac gtg ttc tca tac gca gac gat ccc tgc agc ctc      1728
Val Asp Arg Glu Tyr Val Phe Ser Tyr Ala Asp Asp Pro Cys Ser Leu
                565                 570                 575 act tac ccg cta atg cag aaa ctt aga cac att ctt gta gac cac gct      1776
Thr Tyr Pro Leu Met Gln Lys Leu Arg His Ile Leu Val Asp His Ala
            580                 585                 590 tta gcg gat cca gaa cgc gag gcc aat tcc gcg aca tcg gtt ttc cac      1824
Leu Ala Asp Pro Glu Arg Glu Ala Asn Ser Ala Thr Ser Val Phe His
        595                 600                 605 aaa atc gga gct ttt gaa gcc gag ctg aaa ctg ctc ctc cct aaa gaa      1872
Lys Ile Gly Ala Phe Glu Ala Glu Leu Lys Leu Leu Leu Pro Lys Glu
    610                 615                 620 gta gaa cgc gtc cgg gtt gaa tac gag gaa gga aca tcg gct ata gct      1920
Val Glu Arg Val Arg Val Glu Tyr Glu Glu Gly Thr Ser Ala Ile Ala
625                 630                 635                 640 aac cgg att aag gaa tgt cgg tct tat cca ttg tat cgg ttt gtc cgc      1968
Asn Arg Ile Lys Glu Cys Arg Ser Tyr Pro Leu Tyr Arg Phe Val Arg
                645                 650                 655 gat gag cta aat act gaa ctg ctt act gga gag aat gtt cgg tcg cca      2016
Asp Glu Leu Asn Thr Glu Leu Leu Thr Gly Glu Asn Val Arg Ser Pro
            660                 665                 670
```

```
gga gag gag ttt gat aaa gtg ttc tta gcg att tct gat gga aaa ctt    2064
Gly Glu Glu Phe Asp Lys Val Phe Leu Ala Ile Ser Asp Gly Lys Leu
        675                 680                 685 att gat ccg ttg ttg gaa tgt ctc aag gag tgg aac gga gct ccg gtt    2112
Ile Asp Pro Leu Leu Glu Cys Leu Lys Glu Trp Asn Gly Ala Pro Val
690                 695                 700 tca atc tgt tga                                                     2124
Ser Ile Cys
705
```

<210> SEQ ID NO 4
<211> LENGTH: 707
<212> TYPE: PRT
<213> ORGANISM: Artificial Sequence
<220> FEATURE:
<223> OTHER INFORMATION: AtPA4L cDNA

<400> SEQUENCE: 4

```
Met Glu Leu Cys Asn Gln Asn His Ile Thr Ala Val Ser Gly Asp
1               5                   10                  15

Pro Leu Asn Trp Asn Ala Thr Ala Glu Ala Leu Lys Gly Ser His Leu
                20                  25                  30

Asp Glu Val Lys Arg Met Val Lys Glu Tyr Arg Lys Glu Ala Val Lys
            35                  40                  45

Leu Gly Gly Glu Thr Leu Thr Ile Gly Gln Val Ala Ala Val Ala Arg
        50                  55                  60

Gly Gly Gly Gly Ser Thr Val Glu Leu Ala Glu Ala Arg Ala Gly
65                  70                  75                  80

Val Lys Ala Ser Ser Glu Trp Val Met Glu Ser Met Asn Arg Gly Thr
                85                  90                  95

Asp Ser Tyr Gly Val Thr Thr Gly Phe Gly Ala Thr Ser His Arg Arg
            100                 105                 110

Thr Lys Gln Gly Gly Ala Leu Gln Asn Glu Leu Ile Arg Phe Leu Asn
        115                 120                 125

Ala Gly Ile Phe Gly Pro Gly Ala Gly Asp Thr Ser His Thr Leu Pro
    130                 135                 140

Lys Pro Thr Thr Arg Ala Ala Met Leu Val Arg Val Asn Thr Leu Leu
145                 150                 155                 160

Gln Gly Tyr Ser Gly Ile Arg Phe Glu Ile Leu Glu Ala Ile Thr Lys
                165                 170                 175

Leu Leu Asn His Glu Ile Thr Pro Cys Leu Pro Leu Arg Gly Thr Ile
            180                 185                 190

Thr Ala Ser Gly Asp Leu Val Pro Leu Ser Tyr Ile Ala Gly Leu Leu
        195                 200                 205

Thr Gly Arg Pro Asn Ser Lys Ala Val Gly Pro Ser Gly Glu Thr Leu
    210                 215                 220

Thr Ala Ser Glu Ala Phe Lys Leu Ala Gly Val Ser Ser Phe Glu
225                 230                 235                 240

Leu Gln Pro Lys Glu Gly Leu Ala Leu Val Asn Gly Thr Ala Val Gly
                245                 250                 255

Ser Gly Leu Ala Ser Thr Val Leu Phe Asp Ala Asn Ile Leu Ala Val
            260                 265                 270

Leu Ser Glu Val Met Ser Ala Met Phe Ala Glu Val Met Gln Gly Lys
        275                 280                 285

Pro Glu Phe Thr Asp His Leu Thr His Lys Leu Lys His His Pro Gly
    290                 295                 300
```

```
Gln Ile Glu Ala Ala Ala Ile Met Glu His Ile Leu Asp Gly Ser Ser
305                 310                 315                 320

Tyr Val Lys Glu Ala Gln Leu Leu His Glu Met Asp Pro Leu Gln Lys
            325                 330                 335

Pro Lys Gln Asp Arg Tyr Ala Leu Arg Thr Ser Pro Gln Trp Leu Gly
        340                 345                 350

Pro Gln Ile Glu Val Ile Arg Ala Ala Thr Lys Met Ile Glu Arg Glu
    355                 360                 365

Ile Asn Ser Val Asn Asp Asn Pro Leu Ile Asp Val Ser Arg Asn Lys
370                 375                 380

Ala Leu His Gly Gly Asn Phe Gln Gly Thr Pro Ile Gly Val Ala Met
385                 390                 395                 400

Asp Asn Ser Arg Leu Ala Ile Ala Ser Ile Gly Lys Leu Met Phe Ala
            405                 410                 415

Gln Phe Ser Glu Leu Val Asn Asp Phe Tyr Asn Asn Gly Leu Pro Ser
        420                 425                 430

Asn Leu Ser Gly Gly Arg Asn Pro Ser Leu Asp Tyr Gly Phe Lys Gly
    435                 440                 445

Ala Glu Ile Ala Met Ala Ser Tyr Cys Ser Glu Leu Gln Phe Leu Ala
450                 455                 460

Asn Pro Val Thr Asn His Val Gln Ser Ala Glu Gln His Asn Gln Asp
465                 470                 475                 480

Val Asn Ser Leu Gly Leu Ile Ser Ser Arg Lys Thr Ala Glu Ala Val
            485                 490                 495

Asp Ile Leu Lys Leu Met Ser Thr Thr Tyr Leu Val Ala Leu Cys Gln
        500                 505                 510

Ala Val Asp Leu Arg His Leu Glu Glu Asn Leu Lys Lys Ala Val Lys
    515                 520                 525

Ser Ala Val Ser Gln Val Ala Lys Arg Val Leu Thr Val Gly Ala Asn
530                 535                 540

Gly Glu Leu His Pro Ser Arg Phe Thr Glu Arg Asp Val Leu Gln Val
545                 550                 555                 560

Val Asp Arg Glu Tyr Val Phe Ser Tyr Ala Asp Asp Pro Cys Ser Leu
            565                 570                 575

Thr Tyr Pro Leu Met Gln Lys Leu Arg His Ile Leu Val Asp His Ala
        580                 585                 590

Leu Ala Asp Pro Glu Arg Glu Ala Asn Ser Ala Thr Ser Val Phe His
    595                 600                 605

Lys Ile Gly Ala Phe Glu Ala Glu Leu Lys Leu Leu Pro Lys Glu
610                 615                 620

Val Glu Arg Val Arg Val Glu Tyr Glu Glu Gly Thr Ser Ala Ile Ala
625                 630                 635                 640

Asn Arg Ile Lys Glu Cys Arg Ser Tyr Pro Leu Tyr Arg Phe Val Arg
            645                 650                 655

Asp Glu Leu Asn Thr Glu Leu Leu Thr Gly Glu Asn Val Arg Ser Pro
        660                 665                 670

Gly Glu Glu Phe Asp Lys Val Phe Leu Ala Ile Ser Asp Gly Lys Leu
    675                 680                 685

Ile Asp Pro Leu Leu Glu Cys Leu Lys Glu Trp Asn Gly Ala Pro Val
690                 695                 700

Ser Ile Cys
705
```